United States Patent [19]
Brunner et al.

[11] Patent Number: 5,635,359
[45] Date of Patent: *Jun. 3, 1997

[54] METHOD FOR MEASURING THE ACTIVITY OF ANGIOTENSIN CONVERTING ENZYME IN BIOLOGICAL SAMPLES

[75] Inventors: Hans R. Brunner, Pully; Jurg Nussberger, La Conversion, both of Switzerland

[73] Assignee: B.M.R.A. Corporation B.V., Rotterdam, Netherlands

[*] Notice: The term of this patent shall not extend beyond the expiration date of Pat. No. 5,407,803.

[21] Appl. No.: 270,364

[22] Filed: Jul. 5, 1994

Related U.S. Application Data

[63] Continuation of Ser. No. 830,341, Jan. 31, 1992, Pat. No. 5,407,803.

[30] Foreign Application Priority Data

Feb. 1, 1991 [EP] European Pat. Off. ............ 91810074

[51] Int. Cl.$^6$ .................................... G01N 33/60
[52] U.S. Cl. .......................... 435/7.4; 435/968; 436/504; 436/804
[58] Field of Search ..................... 435/7.4, 7.92, 435/7.93, 7.9, 975, 240.27, 968; 436/548, 804, 504; 530/316, 800, 388.1

[56] References Cited

U.S. PATENT DOCUMENTS 5,407,803  4/1995  Brunner et al. .................... 435/7.4

FOREIGN PATENT DOCUMENTS 273453  7/1988  European Pat. Off. .

OTHER PUBLICATIONS

Goodfriend, T.L., et al., "Antibodies to Bradykinin and Angiotensin: A Use of Carbodiimides in Immunology," *Science* 144:1344–1346, 1964.

Nussberger, J., et al., "True Versus Immunoreactive Angiotensin II in Human Plasma," *Suppl. I. Hypertension* 7:I–1 to I–7, 1985.

Nussberger, J., et al., "Selectivity of Angiotensin II Antisera," *Journal of Immunological Methods* 56: 85–96, 1983.

Poulsen and Jorgensen, "An Easy Radioimmunological Microassay of Renin Activity, Concentration and Substrate in Human and Animal Plasma and Tissues Based on Angiotensin I Trapping by Antibody," *The Journal of Clinical Endocrinology and Metabolism* 39:816–825, 1974.

Poulsen, Knud, "Simplied Method for Radioimmunossay of Enzyme Systems," *The Journal of Laboratory and Clinical Medicine* 78:309–315, 1971.

Nussberger et al., "Angiotensen II Measurement with High–Affinity Monoclonal Antibodies," *Journal of Hypertension* 6 Suppl. 4:S424–S425, 1988.

Nussberger et al., "Measurement of Converting Enzyme Activity by Antibody–Trapping of Generated Angiotensin II," *Am. J. Hypertension* 5:393–398, 1992.

*Primary Examiner*—Marian C. Knode
*Assistant Examiner*—Donna C. Wortman
*Attorney, Agent, or Firm*—Seed and Berry LLP

[57] ABSTRACT

The activity of angiotensin converting enzyme (ACE) is measured in biological samples as body fluids. ACE-activity is estimated in minimally diluted specimens, using the natural substrate angiotensin I at close to physiological concentration. Femtomoles of generated angiotensin II are trapped by specific high affinity monoclonal antibodies and thus protected from degradation by angiotensinases during the incubation step. The same antibodies are subsequently used for quantitation by radioimmunoassay.

18 Claims, 3 Drawing Sheets

METHOD FOR MEASURING THE ACTIVITY OF ANGIOTENSIN CONVERTING ENZYME IN BIOLOGICAL SAMPLES

CROSS-REFERENCE TO RELATED APPLICATION

This application is a continuation of U.S. patent application Ser. No. 07/830,341, filed Jan. 31, 1992, and issued Apr. 18, 1995, as U.S. Pat. No. 5,407,803.

The present invention concerns a new method for measuring the enzyme activity of angiotensin converting enzyme (ACE) in biological samples using angiotensin I as a substrate and a monoclonal antibody for trapping angiotensin II formed from angiotensin I; eventually the angiotensin II is detected by radioimmunoassay (RIA).

According to the state of the art, activity of the angiotensin converting enzyme (ACE) is usually measured in vitro by estimation of products cleaved by the enzyme from synthetic substrates. These substrates have affinities for ACE different from the natural substrate angiotensin I, and insensitive detection systems necessitate millimolar substrate concentrations while physiological angiotensin I concentrations are in the picomolar range.

Products cleaved from these substrates under standardized reaction conditions are quantitated in order to estimate ACE-activity (Cushman D. W., Cheung H. S., Biochem. Biophys. Acta 1971; 250: 261–265; Ryan J. W., Chung A., Ammons C., Carlton M. L., Biochem. J. 1977; 167: 501–504; Piquilloud Y., Reinharz A., Roth M.. Biochem. Biophys. Acta 1970; 206: 136–142). Over the last two decades, ACE-inhibiting drugs became available and today are widely used for the treatment of hypertension and congestive heart failure. Plasma ACE-activity is measured for drug monitoring in patients treated with ACE-inhibitors and conventional methods used so far provided well reproducible results. However, in contrast to such consistency in measurement (precision), absolute ACE-activities were found to differ considerably (accuracy) when measured in a given plasma with different methods (Juillerat L., Nussberger J., Ménard J., Mooser V., Weebet B., Graf P., Brunner H. R., Hypertension 1990; 12: 87–92). Moreover, if the ratio of plasma concentrations of angiotensin (Ang) II to Ang I is used as an indicator of ACE-activity in vivo (Giese J., Rasmussen S., Damkjaer M. N., Ibsen H., J Hypertension 1983; 1 (Suppl. 1): 31–36; Nussberger J., Juillerat L., Perret F., Waeber B., Bellet M., Brunner H. R., Ménard J., Am. Heart J. 1989; 117: 717–722), in vitro different methods of ACE-activity measurement must be applied depending on which particular ACE-inhibitor is monitored in order to obtain appropriate parallelism between results in vivo and in vitro (Juillerat L., Nussberger J., Ménard J., Mooser V., Waeber B., Graf P., Brunner H. R., Hypertension 1990; 12:87–92). Inaccuracy of conventional methods may be due to several reasons: Firstly, substrates used are chemically different from the natural substrate angiotensin I; secondly, insensitive detection systems used to quantitate products cleaved by ACE from these substrates necessitate very high substrate concentrations; thirdly, dilution of biological samples in vitro induces reaction conditions different from those in vivo.

The object of the present invention is to provide a new and accurate method of measurement of ACE-activity which overcomes the above-mentioned difficulties. The subject of the present invention is thus the method for measurement of the enzyme activity of angiotensin converting enzyme (ACE) in a biological sample on basis on cleavage of a substrate by ACE and detecting one of the products cleaved from the substrate, characterized in that angiotensin I (Ang I) as a substrate of ACE and antibodies of a specific affinity for angiotensin II (Ang II) are added to the biological sample, and that Ang II, generated from the reaction of ACE and Ang I, is trapped and protected by said antibodies and the same antibodies are subsequently used for quantitation of Ang II by radioimmunoassay In the method according to the invention, plasma ACE-activity is estimated in minimally diluted specimens, using the natural substrate angiotensin I at close to physiological concentration. Femtomoles of generated angiotensin II are trapped by specific high affinity monoclonal antibodies and thus protected from degradation by angiotensinases during the incubation step. The same antibodies are subsequently used for quantitation by radioimmunoassay (Poulsen K, Jörgensen J. J. Clin. Endocrinol. Metab. 1974; 39: 816–825).

The new assay for ACE-activity measurement quantitates reliably femtomoles of generated angiotensin II in plasma from angiotensin I added at 10 picomolar concentration. The production of high affinity monoclonal antibodies against angiotensin II ($K_d=7\times10^{-11}$M) allowed a quantitive trapping (and thus protection from degrading enzymes) of angiotensin II generated during the incubation step and subsequent radioimmunoassay by simple dilution with labeled angiotensin II.

Using 40 µl of plasma, the detection limit was 20 fmol/ml/min. Normal human plasma had an ACE-activity of 335±83 fmol/ml/min (mean±SD). Precision was characterized by coefficients of variation of less than 11% both within-assay and between-assays. Accuracy of the new method was established by comparing ACE-activity with the ratio of plasma angiotensin II/angiotensin I in plasma obtained from normal volunteers 0.5–24 hours after oral administration of 20 mg enalapril: Percentage ACE-inhibition indicated by both methods was almost identical (r=0.93, n=60, p<0.001). Since the latter ratio appears to reflect in vivo ACE-activity, these results indicate that accurate measurement in vitro of ACE-activity in vivo has been achieved.

BRIEF DESCRIPTION OF THE DRAWINGS

The invention is illustrated in detail by the enclosed drawings, in which.

Figure 1:
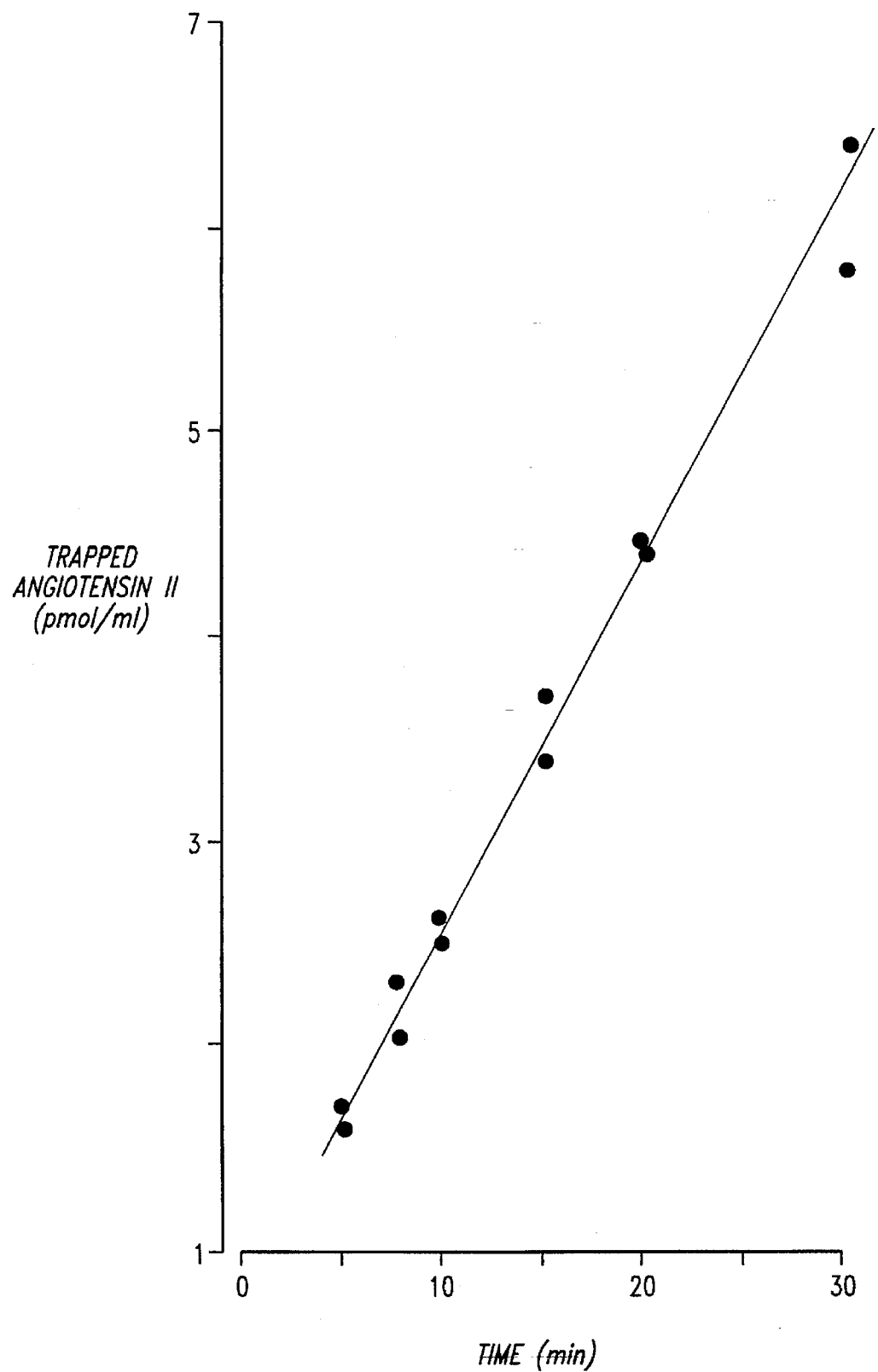
FIG. 1 shows a graph wherein the linearity of generation of angiotensin II in a plasma sample incubated at 37° C. is demonstrated: generated angiotensin II is trapped by added high affinity monoclonal antibodies and protected against enzymatic degradation. Subsequent dilution makes it possible to quantitate angiotensin II radioimanunologically by using these antibodies.

An embodiment of the invention is illustrated by the example below.

EXAMPLE a) Preparation of the Samples
   Study Protocol

Ten normal volunteers aged 20 to 28 years (body weight 63 to 85 kg) participated in the study. On the study day, they came to the hospital at 7 a.m. and were installed in a supine position. At 8 a.m., the subjects ingested 20 mg enalapril, an inhibitor of angiotensin converting enzyme. Venous blood samples were collected before (time 0) and at 0.5, 1, 2, 4, 8 and 24 hours after enalapril intake. The subjects remained in supine position for one hour prior to blood sampling and no food intake was permitted within three hours prior to sampling.

Blood Sampling

For the measurement of ACE-activity, blood samples (5 ml) were collected from the antecubital vein into prechilled glass tubes containing heparin (56 USP) and 25 µl renin inhibitor CGP 29287 (Ciba-Geigy, Basel, Switzerland) at 1 mM in water. Blood was centrifuged at 4° C. and 2000 g for 10 minutes and plasma aliquots of 0.5 ml were snap frozen in liquid nitrogen and stored at −70° C. until analyzed.

For the measurement of Ang II (Nussberger J., Brunner D. B., Waeber B., Brunner H. R., Hypertension 1985; 7 (Suppl. I): 11–17) and immunoreactive Ang I (Nussberger J., Brunner D. B., Waeber B., Brunner H. R., Life Sci. 1988; 42:1683–1688), another 10 ml blood were collected on an inhibitor cocktail containing EDTA and renin inhibitor to prevent degradation and generation of these peptides in vitro. Samples were centrifuged at 4° C. and plasma aliquots of 2.2 ml snap frozen and stored as described above.

b) Material

Monoclonal antibodies against angiotensin (Ang) II can be produced by the somatic cell fusion technique (Köhler G., Milstein C., Nature 1975; 256: 495–497) as previously described in detail (Nussberger J., Mudgett-Hunter M., Matsueda G. R., Haber E., Hybridoma 1984; 3: 373–376) but using SP 2/0 myeloma cells and spleen lymphocytes of a C3H mouse hyperimmunized with Ang II which was coupled by its carboxy-terminus to bovine thyroglobulin (Nussberger J., Matsueda G. R., Re R., Haber E., J. Immunol. Methods 1983; 56: 85–96). For the measurement of ACE-activity in the example below, a high-affinity monoclonal angiotensin II-antibody ("TRAP", $Kd=7\times10^{-11}M$) of the IgG1 class was used which is secreted by the hybridoma cell line "TRAP", which was deposited on Jan. 29, 1991 at the Deutsche Sammlung von Mikroorganismen und Zellkulturen (DSM), Mascheroder Weg 1b, D-3300 Braunschweig. The cell line obtained the deposition number DSM ACC2003. The monoclonal antibody cross reacted with the carboxy-terminal fragments of Ang II at 75–105% and less than 1% with Ang I and amino-terminal fragments. No crossreaction (below $10^{-6}\%$) was found with angiotensinase inhibitors such as tripotassium ethylenediaminetetraacetate (EDTA, purchased from Fluka, Buchs, Switzerland) or bacitracin (Grossmann Pharmaca, Basel, Switzerland).

Albumin buffer consisted of a 0.1M tris buffer (Sigma, St. Louis, Mo.) containing per liter 5 gram heat inactivated bovine serum albumin (Sigma), 20 mmol bacitracin and 200 mg sodium azide (Merck, Darmstadt, Germany). The pH was adjusted to 7.5 at room temperature.

Angiotensin I and angiotensin II standard peptides were purchased from Peninsula Labs (St. Helens, England). $^{125}$I-Ang II was obtained from New England Nuclear Inc. (Boston, Mass.).

c) Measurement of Plasma ACE-activity

All procedures were done in an ice-water bath unless stated otherwise: Plasma was thawed and centrifuged at 4° C. and 40 µl supernatant was pipetted into a small polypropylene tube. Ten microliter monoclonal antibody TRAP (which was secreted from the Hybridoma cell line TRAP DSM ACC2003) was added (mouse ascites diluted 1:8400 in 3M tris buffer at pH 7.3). One picomole angiotensin I was added in 10 microliter albumin buffer containing—for blank determination only—EDTA at 0.2M concentration. After mixing and cold centrifugation in order to concentrate the mixture at the bottom of the tube (1 minute at 2000 g) samples were incubated in a water bath at 37° C. for 20 minutes. Incubation was stopped by returning the samples to the ice-water bath. Forty microliters of albumin buffer without/with 0.2M EDTA was added to blanks/samples in order to equalize conditions. Each tube (total 100 microliters) finally received 1 ml albumin buffer containing 1 fmol $^{125}$I-Ang II (2000 counts per minute) and EDTA at 0.02M concentration. After a 24 hour incubation at 4° C., antibody-bound and free Ang II were separated by adding 0.3 ml water containing 2% dextran-coated charcoal, mixing for 10 minutes, centrifugation at 4° C. (for 20 minutes at 6000 g) and decanting of the supernatant. Supernatant and pellet were counted in a ten-well scintillation counter (GammamasterR, Wallac, Turku, Finland) and generated Ang II was read from a simultaneously established standard curve.

For the standard curve, increasing amounts of unlabeled Ang II ranging from 16 to 4000 fmol in 40 µl pool plasma which contained unmeasurably low endogenous Ang I and Ang II and renin inhibitor CGP 29287 at 0.01 mM concentration; antibody in 3M tris buffer (10 µl) and 1000 fmol Ang I in EDTA-albumin buffer (10 µl) were added in order to obtain identical conditions as for the unknown samples.

Plasma ACE-activity was also measured by an established method using as substrate synthetic carbobenzoxy-Phe-His-Leu at 1.8 mM concentration (Piquilloud Y., Reinharz A., Roth M., Biochem. Biophys. Acta 1970; 206: 136–142). The ratio of the plasma concentrations Ang II/Ang I was used for estimation of ACE-activity "in vivo" (Nussberger J., Juillerat L., Perret F., Waeber B., Bellet M., Brunner H. R., Ménard J., Am Heart J. 1989; 117: 717–722).

Characteristics of Trapping-assay for Plasma ACE-activity

Sensitivity: The present assay is optimized for a final dilution of the monoclonal antibody at 1:924000. The smallest amount of unlabeled Ang II (16 fmol/tube) added to the standard curve results in antibody-binding of 50% of the tracer-angiotensin. This is more than two standard deviations less than tracer binding in the absence of unlabeled Ang II. Thus, the smallest possible amount of Ang II which can be read from the standard slope is 16 fmol. The theoretical detection limit for ACE-activity in a 40 µl plasma sample which was incubated for 20 minutes at 37° C. is 20 fmol/ml/min (16×25/20). The actual detection limit is zero, since EDTA-blanks may contain more than 16 fmol Ang II and these blanks are subtracted from Ang II generated during the incubation.

Specificity: ACE is a relative unspecific enzyme since it cleaves substrates other than Ang I such as bradykinin or substance P. The present assay measures specifically Ang II (carboxyterminal-specific monoclonal antibody) and uses Ang I as substrate under almost physiological conditions. Endogenous Ang II is subtracted as well as Ang II generated in plasma despite renin inhibition and ACE-inhibition by EDTA (blanks).

Precision: Within-assay precision was determined by repeated measurement within a single assay of plasma aliquots containing low, intermediate or high ACE-activity (n=10, each): Results were (mean±SD) 87.3±9.4 fmol/ml/min, 144.9±9.2 fmol/ml/min, 205.5±13.9 fmol/ml/min and 389.0±21.3 fmol/ml/min, respectively. The corresponding coefficients of variation (CV) for within-assay precision were 10.8%, 6.4%, 6.8% and 5.5%. Similarly, a plasma was analyzed on 24 different days and it was found to contain an ACE-activity of 228.6±24.9 fmol/ml/min, i.e. a CV for between-assay precision of 10.9%.

Normal values: Plasma ACE-activity in 22 normal human subjects was found to be 334.7±82.9 fmol/ml/min (Mean±SD) with a range between 178 and 475.

Linearity: The linearity of the enzymatic reaction during incubation at 37° C. was tested by incubating a normal plasma sample for 5, 8, 10, 15, 20 and 30 minutes at 37° C. Results are demonstrated in FIG. 1: There was a good linearity throughout the entire test period.

Accuracy of Trapping Assay

Table 1 demonstrates the effect of the single oral dose of 20 mg enalapril in 10 volunteers on plasma ACE-activity, plasma levels of Ang I and Ang II as well as the ratio of plasma Ang II to Ang I. All parameters reached peak effects at 4 and 8 hours after enalapril administration. ACE-results obtained with the trapping method were well correlated with those obtained by the conventional method (r=0.95, p<0.001, FIG. 2, upper panel); in addition, results of the trapping method (y)—unlike conventionally obtained results—are virtually identical with ACE-activity "in vivo" (x): y=0.82x+4.64 (FIG. 2b).

Figure 2A:
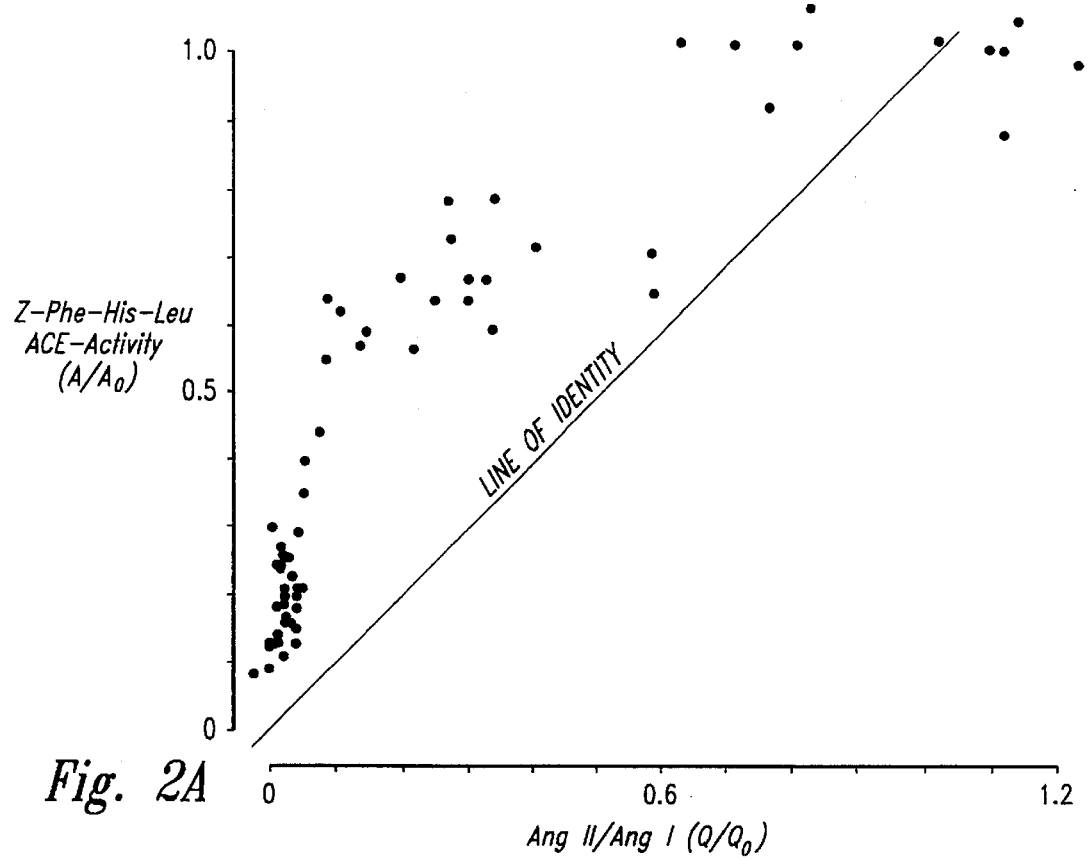
FIGS. 2a and 2b are graphs showing the assessment of converting enzyme (ACE) inhibition in vitro (ordinate) and in vivo (Ang II/Ang I): ACE-activity in the plasma of 10 normal men up to 24 hours after ingestion of 20 mg enalapril (n=60). In vitro measurement by conventional procedures using Z-Phe-His-Leu as a substrate (FIG. 2a) underestimated ACE-inhibition whereas the new trapping method (FIG. 2b) indicated similar ACE-activity in vitro (A) as estimated in vivo (Q) by the ratio of plasma angiotensin II to angiotensin I. Plasma ACE-activity before enalapril ingestion is $A_o$ in vitro and $Q_o$ in vivo.
Figure 2B:
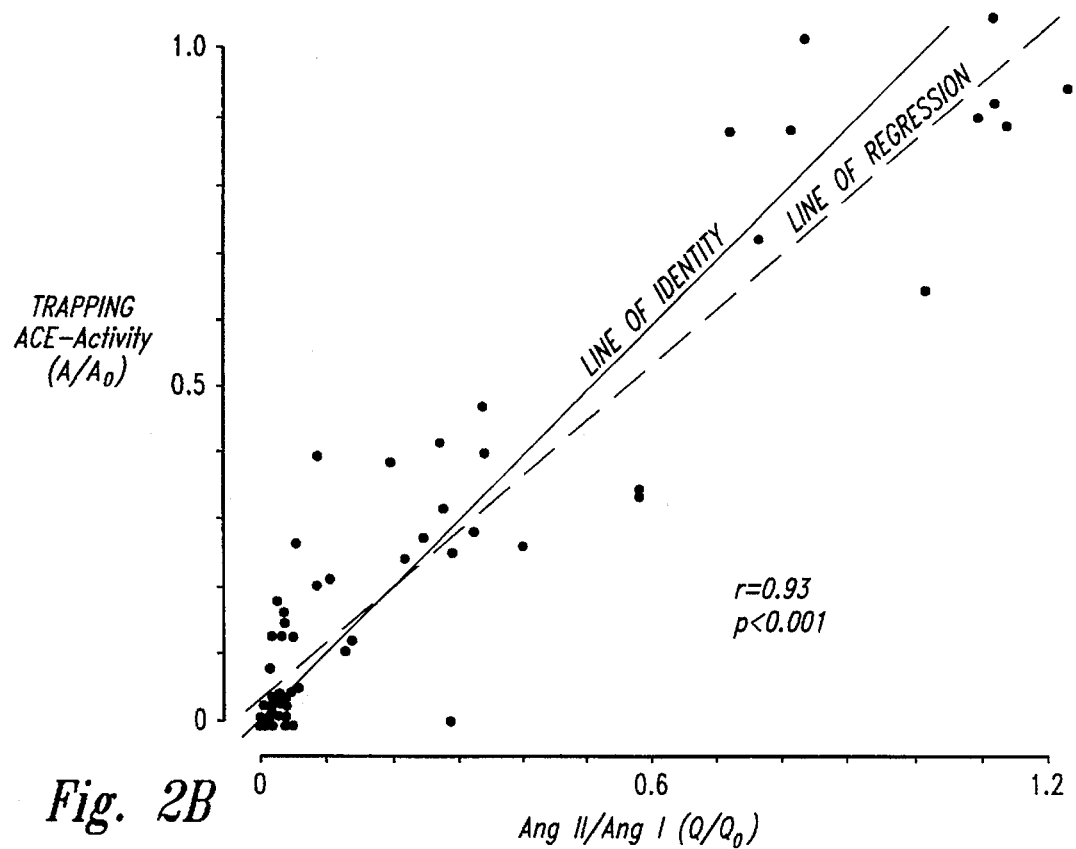
Figure 3:
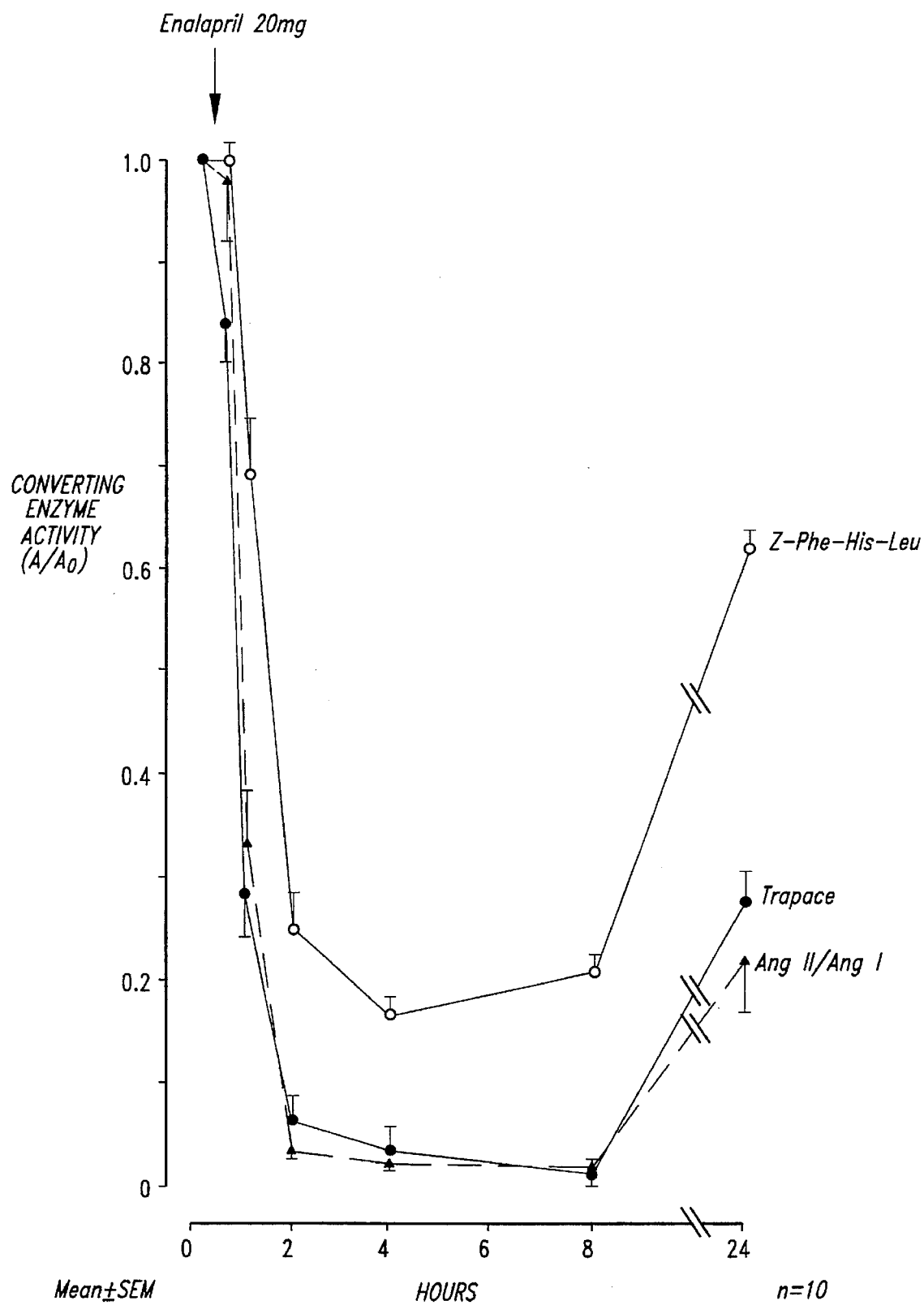
FIG. 3 is a graph showing the in vivo (dashed line) and in vitro (solid lines) plasma converting enzyme (ACE) activity in 10 normal men before and up to 24 hours after ingestion of 20 mg enalapril. In vivo ACE-activity was estimated by the ratio of plasma angiotensin II to angiotensin I (Ang II/Ang I). In vitro measurement using the new trapping assay (Trapace, filled circles) gave virtually identical results as those measured in vivo. Conventional measurement of ACE-activity in vitro using the substrate carbobenzoxy-Phe-His-Leu (Z-Phe-His-Leu, open circles) underestimated ACE-inhibition.

Measured ACE-activities were expressed for every subject as percent of baseline ACE-activity and means±SEM were calculated for each time point (FIG. 2). In vivo ACE-activity (ratio of plasma Ang II to Ang I) reached minima at 4 and 8 hours post enalapril intake with 2.1±0.3 and 2.0±0.4% and on the following morning (24 hours) in vivo ACE-activity was still only 21.9±5.0%. This was in excellent agreement with ACE-activities measured in vitro with the trapping-assay: 3.6±2.4, 1.3±1.3 and 27.4±3.4%. In contrast, the conventional method for ACE-activity 5 measurement in vitro provided different results: At 4, 8 and 24 hours after enalapril administration, plasma ACE-activities were found to be at 16.5±1.7, 20.8±1.7 and 62.6±1.6% of pretreatment values.

Accuracy of test results is a key issue for comparing biochemical effects of different drugs of the same class of therapeutic agents. Most studies involving ACE-inhibitors so far were endorsed by established measurement of plasma ACE-activity using high concentration of substrates with more or less affinity for the ACE (Cushman D. W., Cheung H. S., Biochem. Biophys. Acta 1971; 250: 261–265; Ryan J. W., Chung A., Ammons C., Carlton M. L., Biochem. J. 1977; 167: 501–504; Piquilloud Y., Reinharz A., Roth M., Biochem. Biophys. Acta 1970; 206: 136–142). Recently, studies comparing effects of different ACE-inhibitors in normal volunteers provided evidence for the clear dependency of results on methods used for ACE-measurement and the need for reliable measurement of plasma angiotensin I and II has been emphasized (Juillerat L., Nussberger J., Ménard J., Mooser V., Waeber B., Graf P., Brunner H. R., Hypertension 1990; 12: 87–92). Therefore an assay was developed which could reflect accurately ACE-activity (and ACE-inhibition) as found in the living organism and which would allow to compare the efficacy of different ACE-inhibitors. The ACE-activity measured according to the present invention in vitro under almost physiological conditions is virtually identical with ACE-activity in vivo.

In the plasma samples used in the above example, the ratio of plasma Ang II to Ang I was used to estimate in vivo ACE-activity: It decreased by 98% at peak inhibition and returned to 22% ACE-activity at 24 hours. Very similar results were obtained for plasma ACE-activity measured in vitro with the method according to the invention based on trapping by monoclonal antibodies of generated Ang II (decrease by 99% at peak inhibition and return to 27% ACE-activity at 24 hours). In contrast, the conventional method of ACE-activity estimation provided different results: Peak ACE-inhibition with only 83% decrease from baseline and substantial return towards baseline with 66% ACE-activity at 24 hours. Thus, the new method of ACE-activity measurement according to the invention provided more accurate results than the established method, if the ratio Ang II/Ang I is accepted as a standard.

The new method of ACE-activity measurement in vitro compares favorably with established procedures: Femtomoles rather than nanomoles can be detected which may be helpful for comparison of peak effects of different ACE-inhibitors. The specificity of the procedure is also greatly enhanced since it is based on a monoclonal antibody of unique specificity and affinity for Ang II and the natural substrate Ang I is used under nearly physiological conditions (conventional methods use diluted plasma and extremely high concentrations of substrates of affinities different from that of Ang I and in the presence of high-affinity ACE-inhibitors which may lead to underestimation or overestimation of ACE-inhibition). The Ang I concentration in almost undiluted plasma of the trapping assay is sufficient to warrant linearity of the Ang II production during the incubation step as demonstrated in FIG. 2. The precision of the trapping method is in our hands not better than that of the conventional techniques, but coefficients of variation below 11% for both within- and between-assay precision certainly demonstrate the validity of the new procedure. However, the high accuracy appears to be a major advantage of the trapping method. Finally, equipment needed for the new procedure is that of a routine radioimmunoassay laboratory including a gammacounter. Monoclonal antibodies are obtainable according to Nussberger et al., Hybridoma 1984, 3: 373–376, a monoclonal antibody was deposited at DSM under the above indicated deposition number, other antibodies against Ang II, and labeled and unlabeled angiotensins are commercially available.

In conclusion, the present invention provides a reliable and accurate new method for the measurement of plasma ACE-activity which is based on trapping of generated Ang II during the enzymatic reaction by high-affinity monoclonal antibodies which are subsequently used to quantitate the peptide by radioimmunoassay.

TABLE 1

Plasma converting enzyme activity and angiotensin concentrations in healthy humans after single oral dose of 20 mg enalapril (mean ± SEM, n = 10)

| Time after enalapril intake (mean) | ACE-Activity trapping-assay (fmol/ml/min) | ACE-Activity Conventional assay (nmol/ml/min) | Angiotensin I (fmol/ml) | Angiotensin II (fmol/ml) | Ratio Ang II/Ang I |
|---|---|---|---|---|---|
| 0   | 335 ± 28  | 18.0 ± 1.6 | 8.2 ± 1.7  | 5.2 ± 0.6 | .780 ± .120 |
| 0.5 | 295 ± 27  | 18.1 ± 1.7 | 7.3 ± 1.5  | 4.6 ± 0.5 | .748 ± .101 |
| 1   | 107 ± 17  | 12.1 ± 1.2 | 13.5 ± 3.0 | 2.9 ± 0.5 | .315 ± .094 |
| 2   | 28 ± 8    | 4.5 ± 0.8  | 45.7 ± 12.9| 1.1 ± 0.3 | .029 ± .006 |
| 4   | 15 ± 10   | 3.0 ± 0.4  | 66.8 ± 17.6| 1.0 ± 0.2 | .015 ± .003 |
| 8   | 5 ± 5     | 3.7 ± 0.4  | 76.6 ± 15.9| 1.6 ± 0.4 | .016 ± .003 |
| 24  | 87 ± 10   | 11.2 ± 1.0 | 32.1 ± 6.4 | 3.8 ± 0.5 | .147 ± .027 |

We claim:

1. A method for measurement of the enzyme activity of angiotensin converting enzyme (ACE) in a biological sample on the basis of cleavage of a substrate by ACE and detecting one of the products cleaved from the substrate, characterized by (a) adding angiotensin I (Ang I) as a substrate of ACE to the biological sample, thereby resulting in cleavage of the Ang I to produce Angiotensin II (Ang II), and (b) adding antibodies of a specific affinity for Ang II to the biological sample, and then (c) trapping and protecting by said antibodies the Ang II generated from the cleavage by ACE of Ang I, and then (d) using the same antibodies for quantitation of Ang II by radioimmunoassay.

2. A method according to claim 1 characterized in that the radioimmunoassay is carded out according to the steps of (a) diluting the sample, and adding a defined amount of labeled Ang II, (b) separating antibody-bound and free Ang II, and (c) counting of the radioactivity.

3. A method according to claim 1 or 2 in that the biological sample is a body fluid.

4. A method according to claim 3 characterized in that the biological sample is a plasma sample which was obtained from blood collected in a container containing heparin and a renin inhibitor, and an angiotensinase inhibitor is added to the sample.

5. A method according to claim 1 characterized in that the radioimmunoassay is carded out according to the steps of (a) diluting the sample, and adding a defined amount of labeled Ang II, (b) separating antibody-bound and free Ang II, and (c) counting of the radioactivity, wherein the biological sample is a body fluid.

6. A method according to claim 1 characterized in that the radioimmunoassay is carded out according to the steps of (a) diluting the sample, and adding a defined amount of labeled Ang II, (b) separating antibody-bound and free Ang II, and (c) counting the radioactivity, wherein the biological sample is a plasma sample obtained from blood collected in a container containing hepafin and a renin inhibitor, and wherein an angiotensinase inhibitor is added to the sample.

7. A method according to claim 1, 2, 5 or 6 characterized in that the method is carried out under almost physiological substrate concentrations.

8. A method according to claim 1 characterized in that the radioimmunoassay is carried out according to the steps of (a) diluting the sample, and adding a defined amount of labeled Ang II, (b) separating antibody-bound and free Ang II, and (c) counting the radioactivity, wherein the biological sample is a plasma sample obtained from blood collected in a container containing heparin and a renin inhibitor, wherein an angiotensinase inhibitor is added to the sample, and wherein the method is carried out under almost physiological substrate concentrations.

9. A method according to claim 1, 2, 5, 6 or 8 characterized in that after the addition of Ang I the sample is incubated at 37° C. for 20 min.

10. A method according to claim 1 characterized in that the radioimmunoassay is carded out according to the steps of (a) diluting the sample, and adding a defined amount of labeled Ang II, (b) separating antibody-bound and free Ang II, and (c) counting the radioactivity, wherein the biological sample is a plasma sample obtained from blood collected in a container containing heparin and a renin inhibitor, wherein an angiotensinase inhibitor is added to the sample, wherein the method is carded out under almost physiological substrate concentrations, and wherein after the addition of Ang I the sample is incubated at 37° C. for 20 min.

11. A method according to claim 1, 2, 5, 6, 8 or 10 characterized in that the evaluation of the results is carried out by using a standard curve obtained from the measurement of increasing amounts of unlabeled Ang II ranging from 16 to 4000 fmol in 40 µl albumin buffer in 40 µl plasma, wherein said plasma is originally free of Ang I and Ang II or comprises only an unmeasurable amount of Ang I and Ang II.

12. A method of measuring the in vitro activity of angiotensin converting enzyme (ACE) in a sample of human blood to produce a result that is virtually identical to the corresponding in vivo ACE activity of the sample, comprising:

(a) withdrawing the sample from a human being into a collection device containing a renin inhibitor and a non-inhibiting anti-coagulant;

(b) mixing the sample with a predetermined amount of angiotensin I (Ang I) and an angiotensinase inhibitor, resulting in cleavage of the Ang I to produce angiotensin II (Ang II);

(c) adding antibodies of a specific affinity for Ang II to the sample;

(d) trapping and protecting the resulting Ang II by the antibodies; and (e) using the same antibodies for quantitation of Ang II by radioimmunoassay.

13. A method according to claim 12 wherein the radioimmunoassay is carded out by diluting the sample and adding a defined amount of labeled Ang II, separating antibody-bound Ang II from free Ang II and counting the radioactivity.

14. A method according to claim 12 wherein the renin inhibitor is CGP 29287, the non-inhibitory anticoagulant is heparin and the angiotensinase inhibitor is bacitracin.

15. A method of measuring the in vitro activity of angiotensin converting enzyme (ACE) in a sample of human blood, wherein the method is able to detect ACE activity to about zero fmol/ml/min, comprising:

(a) withdrawing the sample from a human being into a collection device containing a renin inhibitor and a non-inhibiting anti-coagulant;

(b) mixing the sample with a predetermined amount of angiotensin I (Ang I) and an angiotensinase inhibitor, resulting in cleavage of the Ang I to produce angiotensin II (Ang II);

(c) adding antibodies of a specific affinity for Ang II to the biological sample;

(d) trapping and protecting the resulting Ang II by said antibodies; and (e) using the same antibodies for quantitation of Ang II by radioimmunoassay.

16. A method according to claim 15 wherein the radioimmunoassay is carried out by diluting the sample and adding a defined amount of labeled Ang II, separating antibody-bound from free Ang II and counting the radioactivity.

17. A method according to claim 15 wherein the detection limit for ACE-activity in a 40 ml plasma sample is at least 20 fmol/ml/min.

18. A method according to claim 15 wherein the renin inhibitor is CGP 29287, the non-inhibitory anticoagulant is heparin and the angiotensinase inhibitor is bacitracin.

* * * * *

UNITED STATES PATENT AND TRADEMARK OFFICE
CERTIFICATE OF CORRECTION

PATENT NO. : 5,635,359
DATED : June 3, 1997
INVENTOR(S) : Hans R. Brunner and Jurg Nussberger It is certified that error appears in the above-identified patent and that said Letters Patent is hereby corrected as shown below:

In column 7, claim 2, line 31, after "is" delete "carded" and substitute therefor -- carried --.

In column 7, claim 5, line 42, after "is" delete "carded" and substitute therefor -- carried --.

In column 7, claim 6, line 48, after "is" delete "carded" and substitute therefor -- carried --.

In column 7, claim 6, line 53, after "containing" delete "hepafin" and substitute therefor -- heparin --.

In column 8, claim 10, line 21, after "is" delete "carded" and substitute therefor -- carried --.

In column 8, claim 13, line 59, after "is" delete "carded" and substitute therefor -- carried --.

Signed and Sealed this

Thirteenth Day of October 1998

*Attest:*

BRUCE LEHMAN

*Attesting Officer*          *Commissioner of Patents and Trademarks*